(12) United States Patent
Igaki et al.

(10) Patent No.: US 9,220,618 B2
(45) Date of Patent: Dec. 29, 2015

(54) MEDICAL CATHETER DEVICE

(75) Inventors: Keiji Igaki, Kyoto (JP); Hirokazu Yamada, Kyoto (JP)

(73) Assignee: Kyoto Medical Planning Co., Ltd., Kyoto (JP)

( * ) Notice: Subject to any disclaimer, the term of this patent is extended or adjusted under 35 U.S.C. 154(b) by 57 days.

(21) Appl. No.: 13/381,164

(22) PCT Filed: Sep. 9, 2010

(86) PCT No.: PCT/JP2010/005516
§ 371 (c)(1),
(2), (4) Date: May 29, 2012

(87) PCT Pub. No.: WO2011/036850
PCT Pub. Date: Mar. 31, 2011

(65) Prior Publication Data

US 2012/0245669 A1 Sep. 27, 2012

(30) Foreign Application Priority Data

Sep. 25, 2009 (JP) .................... 2009-221434

(51) Int. Cl.
*A61F 2/06* (2013.01)
*A61F 2/958* (2013.01)

(52) U.S. Cl.
CPC .......... *A61F 2/958* (2013.01); *A61F 2002/9583* (2013.01)

(58) Field of Classification Search
CPC .......... A61F 2/958; A61F 2/962; A61F 2/966; A61F 2002/9583
USPC ........ 623/1.11, 1.12, 1.23; 606/194, 198, 108
See application file for complete search history.

(56) References Cited

U.S. PATENT DOCUMENTS

| 5,792,144 A * | 8/1998 | Fischell et al. ............... 606/108 |
| 6,190,393 B1 | 2/2001 | Bevier et al. |
| 2003/0212410 A1 | 11/2003 | Stenzel et al. |

(Continued)

FOREIGN PATENT DOCUMENTS

| JP | 2007125422 | 5/2007 |
| JP | 2008284019 | 11/2008 |

(Continued)

OTHER PUBLICATIONS

European Patent Office, extended European Search Report issued in connection with European Patent Application No. 10818531.5, dated Dec. 10, 2013. (5 pages).

*Primary Examiner* — Katrina Stransky
(74) *Attorney, Agent, or Firm* — K&L Gates LLP

(57) ABSTRACT

Medical catheter apparatus used for implanting a vascular stent into a vessel of a living body comprising a catheter including a distal portion where a balloon attaching a vascular stent is provided, and a sheath into which the catheter is inserted and to be moved relative to the catheter between the section where it covers the balloon on which a vascular stent is mounted and the section where it exposes the vascular stent mounted on the balloon. The sheath comprises a first tubular member covering the distal portion at which the balloon is provided, and a second tubular member covering the proximal portion of the catheter and connected with the first tubular member. The first tubular member is formed of a tubular member capable of flexible deformation and the second tubular member is formed of a tubular member less extensible in the axial direction than the first tubular member.

9 Claims, 5 Drawing Sheets

(56) References Cited

U.S. PATENT DOCUMENTS

2004/0098081 A1* 5/2004 Landreville et al. ......... 623/1.11
2005/0033402 A1 2/2005 Cully et al.

FOREIGN PATENT DOCUMENTS

| WO | 2004066809 | 8/2004 |
| WO | 2009/009636 | 1/2009 |

* cited by examiner

MEDICAL CATHETER DEVICE

CROSS REFERENCES TO RELATED APPLICATIONS

The present application is a national stage of International Application No. PCT/JP2010/005516 filed on Sep. 9, 2010 and claims priority to Japanese Patent Application No. 2009-221434 filed on Sep. 25, 2009, the disclosures of which are incorporated herein by reference.

BACKGROUND

Heretofore, when stenosis occurs in a vessel of a living body, such as a coronary artery, percutaneous transluminal angioplasty (PTA) is performed in which the stenosed portion in the vessel is expanded to improve the blood flow using a medical balloon catheter.

The site once stenosed, however, is known to have high possibility of restenosis or acute occlusion due to intimal dissection even after PTA. To prevent such acute occlusion or restenosis, a tubular shaped stent is implanted at the site following PTA. The stent is in a contracted state when introduced into a blood vessel, and subsequently expanded in diameter so as to be deployed at the intended site scaffolding the vessel wall from its inside.

The stent to be implanted in a blood vessel is inserted and transported to the intended site in the vessel by using a catheter having a balloon which can be dilated with expansion medium supplied thereto. Specifically, the contracted stent is mounted onto the balloon provided at the distal portion of the catheter to be inserted into the blood vessel and transported to the intended site together with the balloon. With the balloon inflation by supplying the expansion medium into it, the stent is expanded in diameter, and consequently deployed at the intended site. The once expanded stent keeps its expanded state even after the balloon is deflated by removal of the expansion medium, thereby scaffolding the implanted site radially to allow fluid path for humor such as blood in the vessel lumen.

The stent is formed into cylindrical shape such that a fluid path is configured through its one end to the other. This stent is contracted to be mounted onto a contracted balloon, and introduced into the blood vessel together with the balloon. Being an independent cylindrical body mounted onto the balloon, however, the stent may be dislocated on the balloon or dislodged from it under force such as friction during delivery. The dislodged stent cannot be expanded by inflating the balloon, resulting in failure to deploy it at the intended site. The stent not dislodged from the balloon but just dislocated relative to the balloon may be subject to the balloon inflation force unequally along its entire length, resulting in its unequal expansion along its entire length. The stent expanded unequally along its length cannot scaffold the vessel wall in the vessel as intended.

In order to prevent dislocation or dislodgement of the stent mounted on the balloon, the present inventor has proposed a catheter apparatus for delivery of a stent wherein a balloon catheter, having a balloon on which the stent is mounted, is inserted into a protective sheath (Patent Document 1). Furthermore, in this catheter apparatus, a holding member holds the one end of the stent to prevent stent dislocation relative to the balloon, when the stent is extruded from the protective sheath to expand in diameter. Since, in this catheter apparatus, the stent mounted on the balloon attached to the distal end of the catheter is covered by the protective sheath when delivered within a vessel such as a blood vessel, stent dislodgement from the balloon can be surely prevented.

CITATION LIST

Patent Literature

PLT 1: WO2004/103450

SUMMARY

Technical Problem

In the catheter apparatus including a protective sheath covering a catheter attaching the above described balloon, like other catheter apparatus, to be smaller diameter compared to the inner diameter of the vessel into which it is inserted is better so as to ensure safety of the vessel and to obtain excellent operability. Therefore, the diameter of the protective sheath needs to be as small as possible, which results that it cannot accommodate a large catheter insertion opening therein.

The catheter having the balloon is provided with a guide wire insertion channel into which a guide wire is inserted, and an expansion medium supplying channel through which an expansion medium used for balloon inflation flows. The catheter provided with several channels needs to have a diameter large enough to accommodate those channels. Moreover, its outer diameter at the section where the stent is mounted is larger than that of other sections, because the tubular stent is attached to the balloon on the catheter there.

In the catheter apparatus employing the protective sheath, large space between the catheter and the protective sheath is not available, because the catheter which cannot be made so small will be inserted into the catheter insertion opening which cannot be made so large. Furthermore, in this kind of catheter apparatus, some portions of the stent or balloon may contact with the inner surface of the sheath, because the balloon is attached to the outer periphery of the catheter which is very close to the protective sheath.

To deploy the stent mounted on the balloon in a blood vessel, the sheath covering the catheter needs to be drawn back after the portion of the catheter, where the stent is mounted, is delivered to the intended site in the blood vessel such that the stent together with the balloon expose from the sheath. During this procedure, when some portions of the stent or the balloon may contact, especially tightly, with the inner surface of the sheath, friction force is caused to restrain relative movement of the sheath and the catheter. This may results that the sheath drawn relative to the catheter is only elongated in the longitudinal direction without uncovering the stent.

A technical object of the present invention is to provide a catheter apparatus in which a vascular stent mounted on a balloon attached to the distal end of a catheter is covered by a protective sheath, allowing relative movement of the catheter and the sheath and consequently uncovering the stent for sure by removal of the sheath.

Further technical object of the present invention is to provide a medical catheter apparatus ensuring its stable insertion into a vessel.

Solution of Problem

To achieve the above-mentioned technical objects, the present invention provides a medical catheter apparatus comprising a catheter attaching a balloon which mounts a cylindrical vascular stent on its outer surface and expands the stent through its inflation with expansion medium, and having an expansion medium supplying channel for supplying an expansion medium for balloon inflation, and a guide wire insertion channel for guide wire insertion, and a sheath into which the catheter is inserted and covering from the distal end of the catheter where the balloon is located through the proximal end of it and moving relatively to the balloon between the section where it covers the balloon attaching the stent and the section where it is intended to uncover the stent. The sheath comprising this catheter apparatus has the first tubular member covering its distal portion where the balloon attaching the stent is located, and the second tubular member connected with the first tubular member and covering its proximal portion. The first tubular member consists of a flexible tubular member allowing flexible deformation and the second tubular member consists of a tubular member which is less-extensible in axial direction compared to the first one.

Preferably, the first tubular member constituting the sheath is formed of a tubular member made of synthetic resin and the second tubular member is formed of a tubular member made of metal having lower extensibility in the axial direction compared to the first tubular member.

Specifically, the second tubular member is formed of a tubular member made of biocompatible stainless steel.

In addition, the first tubular member is preferably formed of a tubular member made of synthetic resin elongated in the axial direction.

Furthermore, the axial length of the second tubular member is preferably longer than that of the first tubular member In the catheter apparatus according to the present invention, a holding member for prevention of relative movement of the sheath and the catheter is provided at the proximal portion of the second tubular member.

Advantageous Effects of Invention

In the medical catheter apparatus according to the present invention, the sheath covering the balloon on which the vascular stent is mounted is constituted of the first tubular member and the second tubular member. The first tubular member placed at the distal side is capable of flexible deformation to be inserted in accordance with shape of a vessel such as a blood vessel. The second tubular member connected to the first tubular member is formed of a tubular member having lower extensibility in the axial direction compared to the first tubular member, this restrains axial elongation of the entire sheath under friction force between the sheath and the catheter caused by removal of the sheath and thus prevents failure in uncovering the stent.

The first tubular member consisted of axially-elongated synthetic resin is capable of flexible deformation to be inserted in accordance with shape of a vessel. Therefore, it restrains axial elongation of the entire sheath resulting in assured uncovering of the stent.

By making the length of the second tubular member, which is formed of a tubular member less extensible in the axial direction compared to the first tubular member, longer than that of the first tubular member, elongation of the entire sheath is further suppressed and thus the stent can be uncovered for sure.

The longer second tubular member enables more stable insertion into a vessel.

In the catheter apparatus according to the present invention, elongation of the entire sheath relative to the catheter under friction force between the sheath and the catheter is restrained and thus failure in uncovering the stent is prevented. This enables the outer diameter of the sheath to be smaller and the entire apparatus thinner in comparison with conventional apparatus.

The catheter and the sheath are held together by a holding member to be inserted into a vessel, thus prevents failure in uncovering the stent.

In the catheter apparatus according to the present invention enables the insertion in accordance with the shape of the vessel as well as delivery and deployment of the vascular stent in the target site.

Additional features and advantages are described herein, and will be apparent from the following Detailed Description and the figures.

DETAILED DESCRIPTION

The present invention is described hereinafter based on illustrative embodiments of catheter apparatus useful to percutaneous transluminal angioplasty (PTA) in which a stenosed portion in a vessel of a living body, such as a blood vessel, is expanded to improve blood flow.

Figure 1:
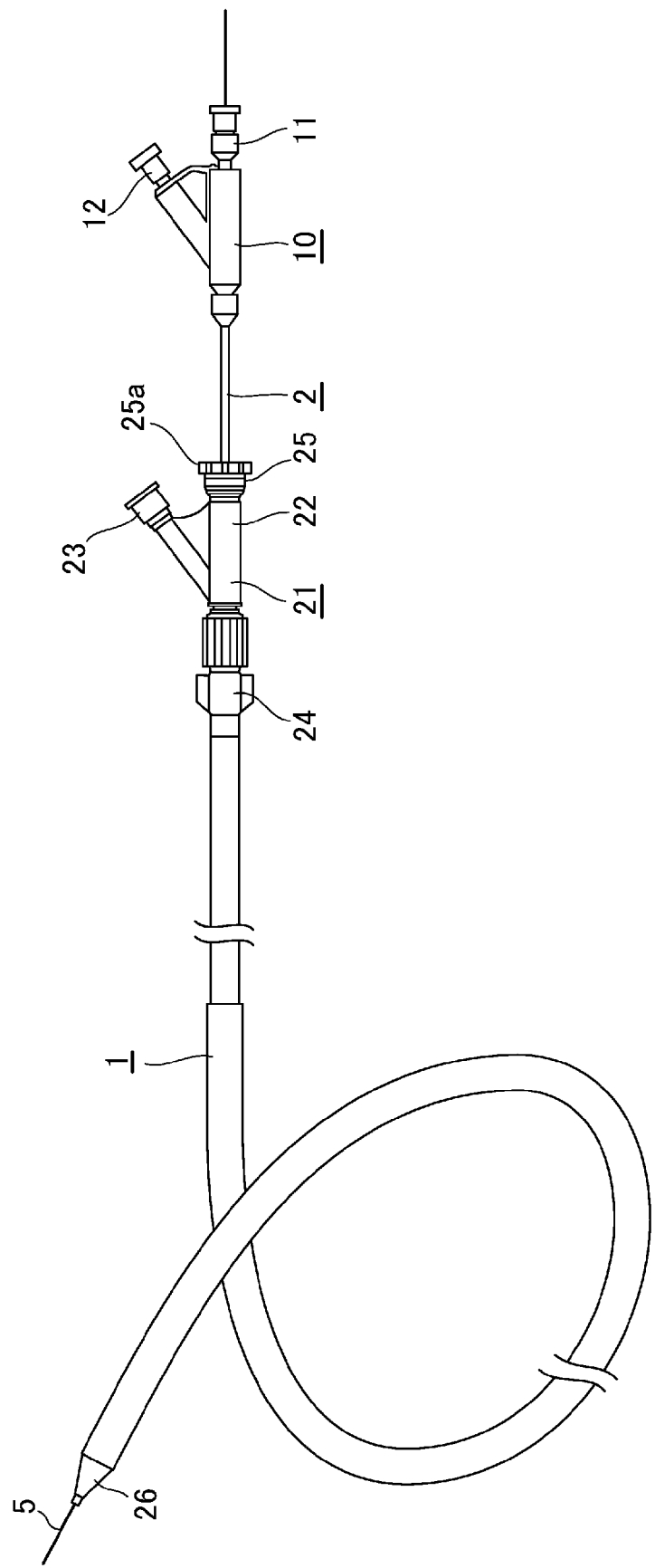
FIG. 1 is a perspective view of a medical catheter apparatus according to the present invention showing its appearance.
Figure 2:
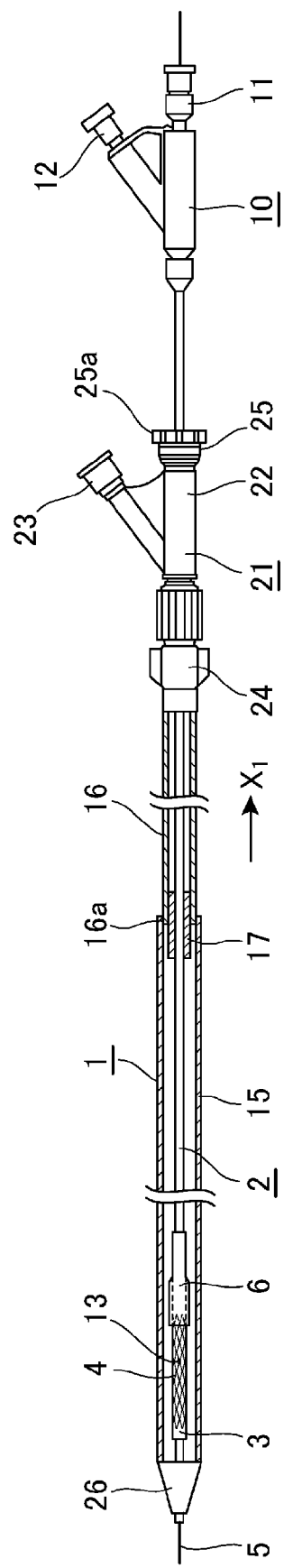
FIG. 2 is a cross-sectional view showing a catheter and a sheath of a catheter apparatus according to the present invention

The catheter apparatus according to the present invention includes a protective sheath 1 and a catheter 2 contained in the sheath 1 with movability to back and forth, as shown in FIGS. 1 and 2.

The catheter 2 constituting the catheter apparatus is, as shown in FIG. 2, an elongated tubular member having diameter of 1 to 2 mm and entire length of 70 to 150 cm. This catheter 2 is formed of a conventional material. Specifically, the material which is flexible enough to deform in accordance with a vessel into which the catheter 2 is inserted and less-extensible in the axial direction is selected to form the catheter 2.

At the distal end of the catheter 2, a balloon 3 which is inflated by an expansion medium such as a contrast medium is provided. On the outer periphery of this balloon 3, a stent 4 to be deployed in the desired site in the blood vessel is mounted. This stent 4 is formed by using, for example, a strand of a biodegradable polymer into a sylindrical shape with a channel therein extending from its one end to the other. This cylindrically shaped stent 4 is mounted on the outer periphery of the balloon 3 and will be expanded in diameter along with the inflation of the balloon 3.

The proximal side of the stent 4 mounted on the balloon 3 is held by a stent holding member 6. The stent holding member 6 is provided so as to prevent the stent 4 from being displaced relative to the balloon 3 during stent expansion, and to ensure reliable expansion of the stent 4 in accordance with the inflation of the balloon 3.

Figure 3:
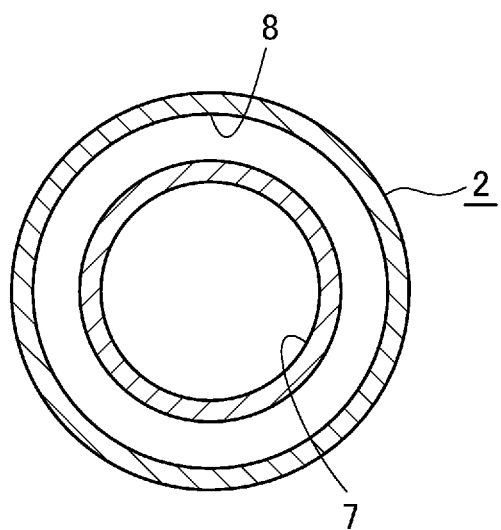
FIG. 3 is a cross-sectional view of a catheter constituting a catheter apparatus according to the present invention.

As shown in FIG. 3, the catheter 2 is provided with a guide wire insertion channel 7 into which a guide wire 5 is inserted for guiding the insertion of this catheter 2 into a blood vessel and an expansion medium supplying channel 8 through which an expansion medium for the expanding the balloon 3 flows. In this embodiment, the guide wire insertion channel 7 and the expansion medium supplying channel 8 extend from the distal end to the proximal end of the catheter 2. As shown in FIG. 3, the guide wire insertion channel 7 and the expansion medium supplying channel 8 are concentrically separated.

A first connecting member 10 is attached to the proximal side of the catheter 2. The first connecting member 10 is provided with a guide wire port 11 which is connected to the guide wire insertion channel 7 and a indeflation port 12 which is connected to the expansion medium supplying channel 8.

The guide wire 5 for guiding the insertion of the catheter apparatus into a blood vessel is inserted into the guide wire insertion channel 7 and pulled out of the catheter 2 through the guide wire port 11. Although not shown in the Figures, an indeflator is connected to the indeflation port 12. An expansion medium for inflating the balloon 3 is supplied from the indeflator. The expansion medium provided from the indeflator enters into the indeflation port 12 and flows in the expansion medium supplying channel 8 via a hole 13 opened at the portion in the catheter 2 where the balloon 3 is attached toward the balloon 3 to inflate it. The stent 4 mounted on the outer periphery of the balloon 3 is expanded in diameter in accordance with the inflation of the balloon 3.

The catheter 2 as stated above is, as shown in FIG. 2, inserted into the protective sheath 1 covering the outer periphery of the catheter 2 from its proximal end to its distal end where the balloon 3 is positioned.

The sheath 1 into which the catheter 2 is inserted is formed by connecting a first tubular member 15 covering the distal side of the catheter 2 provided with the balloon 3 on which the stent 4 is mounted and a second tubular member 16 covering the proximal side of the catheter 2. The first tubular member 15 is formed of a tubular member capable of flexible deformation, and the second tubular member 16 is formed of a tubular member less extensible in the axial direction than the first tubular member 15. Specifically, the first tubular member 15 is formed of a tubular member made of synthetic resin and the second tubular member 16 is formed of a tubular member made of metal having lower extensibility in the axial direction than that of the first tubular member 15.

The catheter apparatus according to the present invention is to be inserted into a blood vessel of a human being, so it should avoid damaging the living body during insertion. Therefore, the first and second tubular members 15, 16 should be formed of a biocompatible material. Specifically, the first tubular member 15 is formed of a polyamide polymer and the second tubular member 16 is formed of a stainless steel, particularly SUS304.

The material of the first tubular member 15 is not limited to a polyamide polymer, but can be other biocompatible synthetic resin as long as it is capable of flexible deformation along the axial direction.

The material of the second tubular member 16, formed of a metal tubular member in this embodiment, is not limited to a metal, but can be a tubular member formed of a synthetic resin with high stiffness as long as it has lower extensibility in the axial direction than that of the first tubular member 15.

The first tubular member 15 covering the distal portion of the catheter 2 provided with the balloon 3 attaching the stent 4 is produced by elongation in the axial direction. Since this first tubular member 15 is elongated in advance in its production process, it can avoid further elongation in the axial direction when axial tension is applied to it.

As shown in FIG. 2, the first tubular member 15 is continuously connected to the second tubular member 16 by fitting the proximal end of the first tubular member 15 to the distal end of the second tubular member 16, to constitute the single sheath 1. The first tubular member 15 is connected to the second tubular member 16 by fitting its proximal end into the outer periphery of the second tubular member 16. In order to prevent disengagement of the connection between the first tubular member 15 and the second tubular member 16, the first tubular member 15 is connected to the second tubular member 16 by bonding them with an adhesive or thermal-welding them in part.

Figure 4:
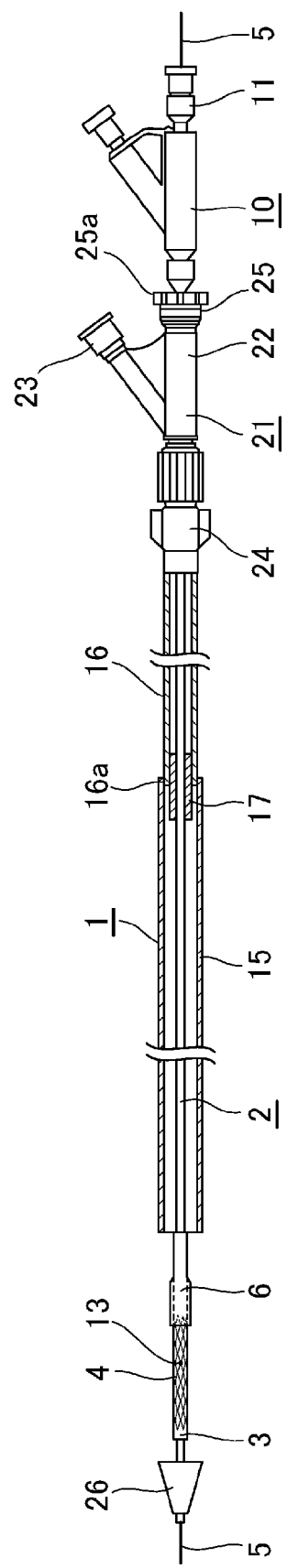
FIG. 4 is a cross-sectional view illustrating a protruded balloon which is mounted on the distal end of a catheter from the distal end of a sheath.

The first tubular member 15 is fitted into the outer periphery of a distal portion 16a of the second tubular member 16, which results that the distal portion 16a is exposed to the lumen of the first tubular member 15, as shown in FIGS. 2 and 4. The catheter 2 inserted into the sheath 1, therefore, contacts with the corner of the distal portion 16a of the second tubular member 16 formed of highly stiff material and may be damaged during its relative movement. To avoid this, as shown in FIG. 2, a protective tube 17 made of a material having higher flexibility than that of the material constituting the catheter 2 is attached to the distal portion of the second tubular member 16. This tube 17 is formed of a polyimide synthetic resin.

In this embodiment, the second tubular member 16 made of the tubular member having lower extensibility in the axial direction than that of the first tubular member 15 is formed as the tubular member longer than the first tubular member 15.

As stated above, the inner diameter of the sheath 1 formed by connecting the first and second tubular members 15, 16 is large enough to permit relative movement of the catheter 2 on the balloon 3 on which the stent 4 is mounted. It is sufficient for the inner diameter of the protective tube 17 to be nearly same in size as the outer diameter of the catheter 2, because only the catheter 2 moves back and forth therein. The outer diameter of the sheath 1 is approximately 1.5 to 3.5 mm so as to be inserted into a blood vessel of a human being.

As stated above and shown in FIG. 2, the sheath 1 formed by connecting the first and second tubular member 15, 16 should be long enough to cover at least the portion of the catheter 2 to be inserted into a blood vessel. A second connecting member 21 from which the catheter 2 is protruded is attached to the proximal side of the sheath 1. The second connecting member 21 is provide with a catheter port 22 from which the catheter 2 inserted into the sheath 1 protrudes and an indeflation port 23 for supplying a liquid such as a saline solution to remove air in the sheath 1.

The second connecting member 21 is attached to the sheath 1 via a connecting hub 24 attached to the proximal portion of the sheath 1. The proximal portion of the catheter port 22 provided in the second connecting member 21 includes a clamp fixing mechanism 25 which provides a fixing mean for fixing the relative movement between the sheath 1 and the catheter 2 protruding from the proximal end of the sheath 1. In this clamp fixing mechanism 25, the screw body is screwed into/out of the catheter port 22 by turning a screw head 25a, thus clamps the catheter 2 and restrains its relative movement to the sheath 1.

The catheter apparatus of the present invention as stated above is assembled by attaching the balloon 3 to the distal portion of the catheter 2, mounting the stent 4 on the outer periphery of the balloon 3, inserting the catheter 2 into the distal portion of the sheath 1, and attaching the first connecting member 10 to the proximal portion of the catheter 2 protruding from the catheter port 22 in the second connecting member 21 connected to the proximal end of the sheath 1.

A guiding member 26 with a tapered shape to guide the insertion of the catheter 2 into a vessel such as a blood vessel is attached to the distal portion of the catheter 2.

In the catheter apparatus according to the present invention, before deployment of the stent 4 mounted on the balloon 3 into a blood vessel, the catheter 2 is put in a state that the balloon 3 on which the stent 4 is mounted is retracted within the sheath 1, which means that the balloon 3 is covered by the first tubular member 15 constituting the sheath 1 as shown in FIG. 2. The proximal portion of the catheter 2 protruding from the catheter port 22 of the second connecting member 21 is clamped by the clamp fixing mechanism 25 so that the relative movement between the sheath 1 and catheter 2 inserted into the sheath 1 is restrained.

In the catheter apparatus according to the present invention, the catheter 2 attaching the stent 4 mounted on the balloon 3 is retracted in and fixed to the sheath 1, and then inserted into a blood vessel of a human being.

The guide wire 5, inserted into the blood vessel in advance, is inserted into the catheter 2 to guide the insertion of the catheter 2 into the blood vessel.

A guide catheter, inserted into the blood vessel in advance, is inserted into the guide wire 5 to guide the insertion of the guide wire 5.

Figure 5:
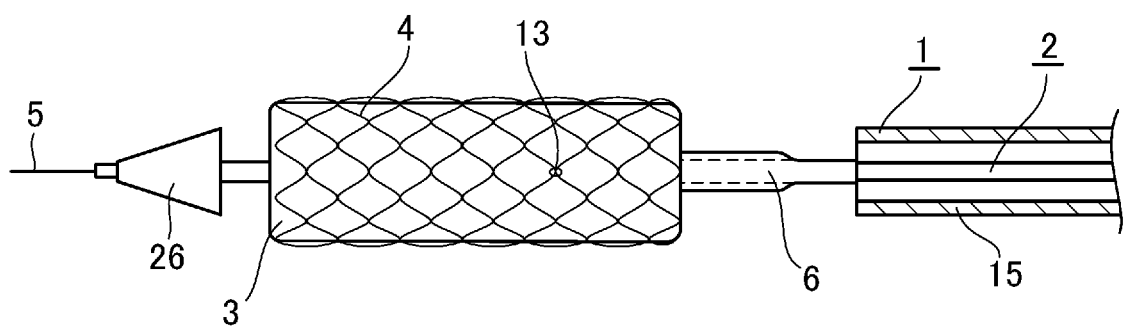
FIG. 5 is a cross-sectional view illustrating a radially expanded stent with an inflated balloon.

When the balloon 3 on which the stent 4 is mounted reaches the intended site, fixation between the catheter 2 and the sheath 1 with the clamp fixing mechanism 25 is released and the sheath 1 is pulled so that the sheath 1 is moved outwardly in the blood vessel relative to the catheter 2, that is, in the direction of the arrow X1 shown in FIG. 2. By pulling the sheath 1 outwardly in the blood vessel, the stent 4 mounted on the balloon 3 is exposed out of the sheath 1 together with the balloon 3, as shown in FIG. 4. Then, by using the indeflator, the expansion medium is supplied to the balloon 3 through the expansion medium supplying channel 8 provided in the catheter 2 and the hole 13 to inflate it. The stent 4 mounted on the balloon 3 is expanded in diameter in accordance with the inflation of the balloon 3 as shown in FIG. 5. The stent 4 thus expanded in diameter scaffolds the inner wall of the blood vessel from the inside. Next, the expansion medium supplied to the balloon 3 is removed through the expansion medium supplying channel 8 to decompress and contract the balloon. When the balloon is contracted in diameter, the stent 4 expanded in diameter is disengaged from the contracted balloon 3 and thus deployed therein to scaffold the inner wall of the blood vessel.

After deployment of the stent 4 in the intended site as explained above, the catheter 2 is pulled to retract the contracted balloon 3 into the sheath 1. After the catheter 2 is pulled into the sheath 1 so that the balloon 3 is retracted within the sheath 1, the catheter 2 and the sheath 1 are finally pulled out of the blood vessel with the aid of the guide wire 5.

If necessary, the catheter 2 and the sheath 1 may be fixed with the clamp fixing mechanism 25.

In the sheath 1 constituting the catheter apparatus according to the present invention, the second tubular member 16 continuously connected to the first tubular member 15 covering the section of the balloon 3 where the stent 4 is mounted, is formed of a tubular member having lower extensibility in the axial direction than that of the first tubular member 15. Therefore, when the sheath 1 is pulled against the catheter 2 to expose the stent 4 on the balloon 3 and subjected to tension, its axial elongation is suppressed and its relative movement to the catheter 2 and reliable exposure of the balloon 3 attaching to the proximal side of the catheter 2 along with the stent 4 are available.

In particular, even in the case that the inner surface of the sheath 1 may contact with the catheter 2 or the stent 4 mounted on the catheter 2 causing friction force between them to restrain relative move of the sheath 1 against the catheter 2 and thus generating tension on the sheath 1, the sheath 1 can avoid its elongation and move smoothly in relation to the catheter 2 to surely expose the stent 4 on the balloon 3 along with the balloon 3 out of the sheath 1.

In the catheter apparatus according to the present invention, since the first tubular member 15 constituting the distal portion of the catheter preceding into the blood vessel during insertion consists of a flexible tubular member allowing flexible deformation, it enables easy deformation according to the shape of the vessel during insertion. It should be noted that even insertion into heavily curved vessel, such as aorta-coronary, is available.

By forming the first tubular member 15 with a tubular member made of axially elongated synthetic resin, further axial elongation of the entire sheath 1 can be suppressed. Therefore, elongation of the sheath 1 relative to catheter 2 is suppressed enabling its smoother move in relation to the catheter 2 with assured exposure of the stent 4 on the balloon 3 along with balloon 3 from the sheath 1.

Furthermore, by forming the second tubular member 16 longer than the first tubular member 15, elongation of the entire sheath 1 can be further suppressed.

In this invention, insertion and removal of the sheath 1 and catheter 2 is safely and easily performed, because, if necessary, they are fixed by the clamp fixing mechanism 25 as a fixing means.

The material for the tubular member 15 is not limited to the above described materials, other materials which are capable of flexible deformation is available. Similarly, the second tubular member 16 is not limited to the above described materials, other materials which are less-extensible in the axial direction than the tubular member 15 is available. The catheter apparatus in this invention, however, is intended for insertion into a vessel in a living body, the tubular member 15, 16 should be desirably made of biocompatible material.

REFERENCE SIGNS LIST 1 sheath
2 catheter
3 balloon
4 stent
5 guide wire
15 first tubular member
16 second tubular member
25 clamp fixing mechanism It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

What is claimed is:
1. A medical catheter apparatus comprising:
a catheter including: an outer periphery on which a cylindrical vascular stent is to be mounted, a distal side attaching a balloon which is to be inflated with supply of an expansion medium to axially expand the stent, an inner lumen provided with at least an expansion medium supplying channel for supplying an expansion medium to expand the balloon, and a guide wire insertion channel for inserting a guide wire, and a sheath into which the catheter is inserted, the sheath having a distal end and a proximal end, the sheath covering the outer periphery of the catheter from the distal side where the balloon attaching the vascular stent is positioned to a proximal side, and the sheath being configured to move relative to the catheter between a first section where the sheath is covering the balloon attaching the vascular stent and a second section where the sheath is exposing the vascular stent attached to the balloon, wherein:

the sheath comprises a first tubular member covering the distal side of the catheter where the balloon attaching the stent is provided, and a second tubular member connected with the first tubular member and covering the proximal side of the catheter, the first tubular member is formed of a tubular member made of an axially-elongated synthetic resin and capable of flexible deformation, the second tubular member is formed of a tubular member that is less extensible in an axial direction than the first tubular member, a proximal end of the first tubular member is fitted to a distal end of the second tubular member, a proximal end of the second tubular member constitutes a proximal end of the sheath, and a distal end of the first tubular member constitutes the distal end of the sheath.

2. The medical catheter apparatus according to claim 1, wherein the first tubular member is formed of a tubular member made of a synthetic resin and the second tubular member is formed of a tubular member consisting of a metal less extensible in the axial direction than the first tubular member.

3. The medical catheter apparatus according to claim 1, wherein the second tubular member is formed of a tubular member made of a stainless steel having biocompatibility.

4. The medical catheter apparatus according to claim 1, wherein an axial length of the second tubular member is longer than that of the first tubular member.

5. The medical catheter apparatus according to claim 1, wherein the proximal end of the first tubular member is fitted into an outer periphery of the distal end of the second tubular member.

6. The medical catheter apparatus according to claim 1, wherein the first tubular member is bonded to the second tubular member.

7. The medical catheter apparatus according to claim 1, comprising a protective tube attached to the distal end of the second tubular member, wherein the protective tube is provided between the catheter and the second tubular member.

8. The medical catheter apparatus according to claim 7, wherein the protective tube comprises a polyimide material.

9. The medical catheter apparatus according to claim 1, wherein a stent holding member formed of a material is provided at the distal end of the catheter and has a first end fitted over the stent and a second end fitted over the catheter to prevent relative displacement between the catheter and the balloon during stent operation.

* * * * *